US012667281B2

(12) United States Patent
Gyger et al.

(10) Patent No.: US 12,667,281 B2
(45) Date of Patent: Jun. 30, 2026

(54) METHOD FOR MONITORING A RECUMBENT PATIENT TO OBTAIN INFORMATION ON A BODY POSITION OF THE PATIENT

(71) Applicant: QUMEA AG, Solothurn (CH)

(72) Inventors: Cyrill Gyger, Solothurn (CH); Jonas Reber, Grafenried (CH); Philipp Rebsamen, Kerzers (CH)

(73) Assignee: QUMEA AG, Solothurn (CH)

( * ) Notice: Subject to any disclaimer, the term of this patent is extended or adjusted under 35 U.S.C. 154(b) by 961 days.

(21) Appl. No.: 17/572,398

(22) Filed: Jan. 10, 2022

(65) Prior Publication Data

US 2022/0218231 A1 Jul. 14, 2022

(30) Foreign Application Priority Data

Jan. 11, 2021 (CH) .......................................... 14/21

(51) Int. Cl.
*A61B 5/113* (2006.01)
*A61B 5/00* (2006.01)

(52) U.S. Cl.
CPC .............. *A61B 5/113* (2013.01); *A61B 5/445* (2013.01); *A61B 5/7264* (2013.01); *A61B 5/7275* (2013.01)

(58) Field of Classification Search
CPC ..... A61B 5/113; A61B 5/1116; A61B 5/0507; A61B 5/1118; A61B 5/1123; A61B 5/445; A61B 5/7275
See application file for complete search history.

(56) References Cited

U.S. PATENT DOCUMENTS

| | | | |
|---|---|---|---|
| 2015/0109442 A1 | 4/2015 | Derenne et al. | |
| 2016/0317099 A1* | 11/2016 | Kawai | A61B 5/4809 |
| 2016/0377705 A1 | 12/2016 | Zack et al. | |
| 2017/0014089 A1* | 1/2017 | Murakami | A61B 5/024 |

(Continued)

FOREIGN PATENT DOCUMENTS

| | | |
|---|---|---|
| EP | 2 715 695 B1 | 3/2016 |
| EP | 3 428 675 B1 | 5/2020 |
| WO | WO2012/158840 A1 | 11/2012 |

OTHER PUBLICATIONS

Extended European Search Report issued Jun. 21, 2022 in corresponding European Application No. 22150757.7.

(Continued)

*Primary Examiner* — Abid A Mustansir
(74) *Attorney, Agent, or Firm* — Birch, Stewart, Kolasch & Birch, LLP

(57) ABSTRACT

A method for monitoring a recumbent patient to obtain information on a body position of the patient comprises the steps of emitting electromagnetic waves by a sender (11) arranged in a distance from the patient, receiving electromagnetic waves reflected by the patient by a receiver (12, 13, 14) arranged in a distance from the patient, determining a movement activity level from an amplitude and/or phase of the received electromagnetic waves, classifying the activity level into at least one high activity level class and into at least one low activity level class and analyzing the amplitude and/or phase of the received electromagnetic waves relating to an activity level classified in the at least one low activity level class to obtain the information on the body position of the patient.

18 Claims, 3 Drawing Sheets

(56)  References Cited

U.S. PATENT DOCUMENTS

| 2018/0049669 | A1* | 2/2018 | Vu ........................ A61B 5/0507 |
| 2018/0120420 | A1* | 5/2018 | McMahon .............. G01S 13/62 |
| 2018/0192919 | A1 | 7/2018 | Nakayama et al. |
| 2019/0117130 | A1 | 4/2019 | Al-Alusi |
| 2020/0383611 | A1 | 12/2020 | Inoue |
| 2021/0197834 | A1 | 7/2021 | Shaker et al. |

OTHER PUBLICATIONS

Shichao Yue, et al., "Body Compass: Monitoring Sleep Posture with Wireless Signals" Proc. ACM Interact. Mob. Wearable Ubiquitous Technol., vol. 4, No. 2, Article 66, Jun. 2020.
Liu et al., "Monitoring Vital Signs and Postures During Sleep Using WiFi Signals", IEEE Internet of Things Journal, vol. 5, No. 3, Jun. 2018, pp. 2071-2084.
Piriyajitakonkij et al., "SleepPoseNet: Multi-View Learning for Sleep Postural Transition Recognition Using Uwb", Journal of Latex Class Files, vol. 14, No. 8, Aug. 2015, pp. 1-11.

* cited by examiner

METHOD FOR MONITORING A RECUMBENT PATIENT TO OBTAIN INFORMATION ON A BODY POSITION OF THE PATIENT

TECHNICAL FIELD

The invention relates to a method for monitoring a recumbent patient to obtain information on a body position of the patient. The invention further relates to a method for obtaining information for assessing a patient's risk for bedsore and to a system for monitoring a recumbent patient to obtain information on a body position of the patient.

BACKGROUND ART

There are situations where the identification of the body position of a recumbent person is required or helpful, especially in the domain of health care. Such information may be helpful to diagnose or treat conditions such as sleep disorders or orthopedic disorders and in particular to identify and mitigate the risk of bedsore (decubitus).

Decubitus or pressure ulcers are one of the biggest nursing problems nowadays. Prevention of pressure ulcers is enormously important, since a pressure ulcer can cause serious secondary diseases such as chronic wounds or infections. In addition, affected patients can get into a negative spiral, as mobility counteracting the pressure ulcer decreases with increasing severity of a pressure ulcer.

Appropriate mobilization of the patient is crucial to prevent pressure ulcers. It must be ensured that there is a regular change of body position and no parts of the body are subjected to pressure for a prolonged period of time. Usually, corresponding measures are taken based on the individual nursing history. Nevertheless, technological aids may be used to support the anamnesis.

The required mobilization and repositioning can be carried out by the patient himself or herself, with manual support by the nursing staff or with the aid of technological aids such as alternating pressure and soft positioning mattresses.

Technological aids to identify the recumbent patient's body position include sensor mattresses or sensor inserts to be positioned on or under the patient's mattress (cf. Mobility Monitor as developed by compliant concept, Fehraltorf, Switzerland or products offered by Early Sense, Ramat Gan, Israel). Further aids include wearables (offered e. g. by Leaf Healthcare, acquired by Smith & Nephew, London, United Kingdom) or imaging processes as described in US 2015/109442 A1 (Stryker Corp.).

EP 2 715 695 B1 (Philips) relates to an apparatus and a method for the detection of the body position while sleeping, based on reflected IR light from the person's body under the blanket. Basically, the reflected intensity is analyzed to obtain information on the body position. In order to improve the determination, acoustical information and/or information on the breathing amplitude may be used. In addition, information which is available due to simultaneous actigraphy processing may be taken into account.

EP 3 428 675 B1 (Hill-Rom Services, Inc.) relates to patient support surfaces such as mattresses, having immersion sensors. These sensors are part of a radar system and detect objects at a range of about 2 centimeters or less. Based on the determined immersion, patient motion may be caused by changing inflation pressures of various bladders supporting the patient. The body position of the patient, including the location of the patient's legs, arms, trunk pelvis and head, may be identified by using body contour mapping. This allows for determining whether the patient is at risk of developing pressure ulcers.

The existing solutions are based on sensors that are arranged in close neighbourhood to the patient to be monitored and/or they are not fully satisfactory with respect to the precision of the acquired data, especially when the patients are covered, e. g. by bed sheets.

SUMMARY OF THE INVENTION

It is the object of the invention to create a method for monitoring a recumbent patient to obtain information on a body position of the patient that does not bother the patient and provides accurate results.

The solution of the invention is specified by the features of claim 1. According to the invention, the method comprises the steps of:

a) emitting electromagnetic waves by a sender arranged in a distance from the patient;

b) receiving electromagnetic waves reflected by the patient by a receiver arranged in a distance from the patient;

c) determining a movement activity level from an amplitude and/or phase of the received electromagnetic waves;

d) classifying the activity level into at least one high activity level class and into at least one low activity level class;

e) analyzing the amplitude and/or phase of the received electromagnetic waves relating to an activity level classified in the at least one low activity level class to obtain the information on the body position of the patient.

The Information on the body position obtained by the inventive method may include specific information on the position (e. g. supine, lateral left, lateral right, prone, etc.) as a function of time or statistical information relating to the body position, e. g. the frequency of the assumed positions and/or of a repositioning of the body.

The recumbent patient may be lying, e. g. in a bed, in particular during rest times or sleep. As well, the recumbent patient may be sitting, e. g. in a chair. In both cases, the patient does not substantially change his or her location during monitoring but exhibits movements when changing position and micro-movements related to physiological activities such as breathing, heartbeat or digestion.

In first embodiments of the inventive method, the movement activity level is determined based on solely the amplitude of the received electromagnetic waves. In particular, this amplitude is compared to the amplitude of the waves emitted by the sender. This comparison yields information on the absorption and reflection of the electromagnetic waves. It may thus be an indication of the absorption and reflection properties of objects in the monitored space.

In second embodiments of the inventive method, the movement activity level is determined based solely on phase information of the received electromagnetic waves. In particular, a change in phase between the emitted and received waves is compared. This yields in particular information related to movements of the objects in the monitored space.

In third embodiments of the inventive method, the movement activity level is determined based on the amplitude as well as on the phase of the received electromagnetic waves.

In all three embodiments, the information on the body position of the patient may be obtained from the same information (i. e. amplitude and/or phase) as used for determining the activity level or from different information relating to the received electromagnetic waves. Furthermore, the movement activity level and/or the information on the body position may be obtained from data that is obtained by preprocessing the amplitude and/or phase information of the received electromagnetic waves. In this context, distance, velocity and/or acceleration values may be obtained from the amplitude and/or phase of the received electromagnetic waves, and such values may be used as a basis for further processing.

The at least one low activity level class may relate to an inactive patient showing no substantial gross motor movements but only micro-movements relating to body functions such as breathing, heartbeat and digestion. The at least one high activity level class may relate to a patient showing gross motor movements, including e. g. movements of the limbs, e. g. movements that are related to a repositioning of the patient's body.

More than two activity level classes may be defined, wherein one or several of the classes are considered to be low activity level classes, considered to obtain the information on the body position of the patient.

In particular, the information on the body position of the patient is obtained exclusively based on values relating to one low activity level class or several low activity level classes, without considering values relating to one high level activity class or several high level activity classes. Preferably, the classes are defined such that all gross motor movements that may relate to a repositioning lead to classifying the related activity level into a high activity level class, such that the information on the body position of the patient is exclusively obtained from values relating to phases without repositioning movements.

In particular, the body position of the patient is identified based on the signal characteristics of the received electromagnetic waves. The body position of a patient greatly affects the absorption and reflection characteristics for electromagnetic waves. As an example, in case of a radar arranged vertically above a patient, the total amplitude of the reflected electromagnetic waves will be substantially bigger with a supine patient than with a patient in a lateral lying position. Similarly, the phase of the reflected signal may be affected differently in different lying positions. After all, movements along a beam direction of the sender lead to a substantially larger compression or stretching of the signal than movements having only a small component along the beam direction. Accordingly, the reflected waves allow for a reliable identification of the patient's body position and/or changes therein. Distinguishing between periods of high (motional) activity and periods of low (motional) activity and taking into account information obtained from the low activity periods improves the identification of the body position. Furthermore, potential repositioning events are identified as they coincide with a high activity level and the repositioning just needs to be confirmed by comparing the low activity signals prior to the event to the low activity signals after the event.

An inventive system for monitoring a recumbent patient to obtain information on a body position of the patient comprises

- a) a sender for emitting electromagnetic waves, the sender being arranged in a distance from the patient;
- b) a receiver for receiving electromagnetic waves reflected by the patient, the receiver being arranged in a distance from the patient;

- c) a first processor adapted to determine a movement activity level from an amplitude and/or phase of the received electromagnetic waves;
- d) a classifier adapted to classify the activity level into at least one high activity level class and into at least one low activity level class; and
- e) a second processor adapted to analyze the amplitude and/or phase of the received electromagnetic waves relating to an activity level classified in the at least one low activity level class to obtain the information on the body position of the patient.

Preferably, the sender and the receiver are arranged in a common unit. More than one sender and/or more than one receiver may be used depending on the employed electromagnetic waves and the desired information.

The sender(s) and receiver(s) are arranged in a distance from the patient. In particular, the distance of the sender(s) and the receiver(s) from the patient is at least 1 m, preferably at least 2 m. Accordingly, they do not bother the patient and there is no need to attach electronics to the patient (in contrast to e. g. wearables). Preferably, the sender and receiver are independent from patient-specific installations such as (hospital) beds or chairs. Most preferably, the sender and receiver are part of an installation that is fixedly arranged in the room, e. g. attached to the ceiling or a wall. It is advantageous if the monitoring volume of the installation covers several or all potential patient sites, e. g. spaces where beds are placed in a room. This allows for a very flexible use and dispenses with physical rearrangement of the monitoring installation. Furthermore, being able to monitor several patients with a single device reduces infrastructure expenses.

The information obtained from the inventive method and system may be used in particular for medical purposes, including anamnesis, diagnosis and therapy. One application of the inventive method is the identification and mitigation of bedsore risk. Accordingly, a preferred method for obtaining information for assessing a patient's risk for bedsore comprises the following steps:

- a) obtain information on a body position of the patient using the inventive method presented above at successive points in time; and
- b) processing the information to obtain at least one of the following:
  - a frequency of repositioning activities of the patient;
  - a distribution of body positions assumed by the patient.

Both results may be combined. As an example, a risk of bedsore is indicated if the frequency of repositioning falls below a threshold minimum frequency or if the time the user assumes a certain body position takes up more than a certain maximum proportion of the total monitoring time (even when the frequency of repositioning is high).

In particular, electromagnetic waves are sent and received regularly, with a temporal resolution of several seconds or better, in order to ensure that potential repositioning events are captured. Depending on the signal characteristics that are employed to determine the body position, a certain temporal resolution might be needed. As an example, to resolve heartbeat or breathing movements or to employ characteristics that are linked to these micro-movements, the temporal resolution should match the corresponding timescale.

The scope of the method is not limited to this application. It can be used as well for the diagnosis or therapy for sleep disorders or orthopedic disorders. One application is the monitoring of infants in order to detect or avoid a prone sleep position to reduce the risk for SIDS. Furthermore, the obtained information may provide indications with respect to the physical constitution of the patient and other health risks.

The inventive system may be used to obtain further information on the patient, e. g. relating to attempts to stand up, falls, unrest, etc.

Preferably, the classified activity levels are assigned to consecutive time intervals. Accordingly, each point in time is assigned to a certain time interval, wherein the time interval is assigned to an activity level. The defined time intervals may have a certain minimum duration in order to avoid rapid changes between different activity levels, e. g. due to very short activity peaks (caused by actual movements of short duration or false positives due to measurement errors, stray signals, etc.), thus facilitating the following analysis.

Because information relating to gross movements might substantially complicate the determination of the body position, it is prudent to assign a lower activity level to a time interval only after a low movement activity level has been determined for a certain first predetermined time. In contrast, for the same purpose a higher activity level may be assigned to a time interval immediately or after the movement activity level has been classified into the higher activity level for a second predetermined time that is shorter than the first predetermined time. A certain interval prior to the assignment of the higher activity level may be retroactively assigned to this higher activity level in order to avoid signals originating from gross movements affecting the further processing of the low activity signals.

Preferably, for obtaining the information on the body position of the patient a signature of a temporal progression of values obtained from the amplitude and/or phase of the received electromagnetic waves relating to the activity level classified in the at least one low activity level class is obtained and the obtained signature is compared to stored signatures obtained for past time intervals.

For example, the signatures may relate to amplitudes, phases or frequencies as well as periodic or a-periodic changes therein as well as results obtained from processing these quantities. They may be represented by or defined by certain key figures obtained from the related data, by the data itself or by any suitable representation thereof, e. g. by "fingerprint" vectors. They may be identified by standard pattern recognition methods or using a machine learning approach. The identification may be based on statistical information on the analyzed signal, on other data derived from the signal or on the signal itself.

Preferably, at least some of the stored signatures are assigned to specific body positions. This allows for deriving the body position based on the obtained signature.

Different approaches for enabling such an assignment are available:

In a preferred embodiment, the assignment is based on a (supervised) machine learning approach, the training data including various captured or simulated signatures and the assigned body positions.

The assignment may be based on a training phase where the body positions have been identified by other means, such as pressure sensors, video data, acoustical information or data obtained from wearables; the training phase may relate to the same patient and/or different patients.

The assignment may be based on manually entered information, e. g. by a caregiver, during a setup or training phase, etc.

In some applications, e. g. assessing the risk for bedsore, where the actual position may be less relevant than the frequency of position changes, it may not be necessary to assign the signatures to body positions. It may be assumed that signatures that substantially differ from each other will relate to different body positions.

Preferably, the movement activity level is obtained based on a temporal variance of a value obtained from the amplitude and phase of the received electromagnetic waves.

In particular, the variance of properties (such as phase and amplitude) of the complex signal or values obtained from these properties is analyzed. Nevertheless, the amplitudes and phases may be analyzed in more detail to obtain the movement activity level.

In particular, the value is obtained by integrating the amplitude and phase information received from a certain spatial volume (e. g. within a designated boundary box). Depending on the available information, the volume may be defined e. g. by angular ranges, e. g. for the azimuthal angle and/or the inclination, and/or by a range for radial distance.

In a preferred embodiment, the movement activity level is obtained from the (relative) variance of the velocity obtained from the received electromagnetic waves. In particular, this measure may be obtained by calculating the index of dispersion (DI) of range-Doppler matrices of consecutive frames. This yields an indication about the rate of change in the velocity frequency and thus an excellent movement detector.

Preferably, these values are continuously calculated for each frame of the measurement and stored in a rolling slow-time window (with a length of e. g. 1 s). Additionally, a suitable filter may be applied to smoothen the signal. The movement activity level is then obtained from the average movement index of the rolling window.

Preferably, the electromagnetic waves are radio waves and the sender and receiver are part of a radar system, in particular of a wideband radar system.

Depending on the chosen frequency, energy and material properties, radio waves can penetrate objects such as bed sheets and thus allow for precise monitoring of the patient. At the same time it is not required to generate a representational image of the patient in order to be able to obtain the desired information, thus safeguarding the patient's privacy.

A wideband radar system is a radar system having a bandwidth of at least 100 MHz. In a preferred embodiment, the wideband radar system is an ultra-wideband (UWB) radar system. Such systems have a bandwidth exceeding the lesser of 500 MHz or 20% of the arithmetic center frequency.

Preferably, the center frequency of the wideband or ultra-wideband radar system is in the range of 2-75 GHz. Advantageously, the range resolution of the radar system is 5 mm or better.

Wideband or ultra-wideband radar systems as well as center frequencies in the given range allow for high resolution, sufficient penetration of objects such as bed sheets and sufficient reflection from the body of the patient to be monitored.

In a preferred embodiment, the wideband radar system is a MIMO (multiple-input multiple-output) radar system, featuring a number of transmitting antennas sending different transmitting signals (in particular orthogonal or intermittent signals) as well as a number of receiving antennas receiving signals from different transmitting antennas. Signals relating to different transmitting antennas may be extracted from the received signals using matched filters. MIMO radar systems may be built compactly, and they offer improved spatial resolution and Doppler resolution compared to 1D systems.

In particular, for spatial resolution, direction of arrival (DoA) values (alternative term: angle of arrival AoA) may be obtained from the phase difference and/or from the time difference of signals received from different receiving antennas. Knowing the DoA values (with respect to a certain reference point) as well as the distances from the individual antennas the 2- or 3-dimensional position of a target is defined. In principle, the signals from any number of antennas being adapted to receive signals from the search area may be utilized to obtain position information. With respect to stationary or slowly moving objects, multiple signals from the same antenna, taken during a certain time interval, may be utilized.

In order to be able to obtain the direction of arrival, the receiving positions of the at least two receiving antennas are arranged in a certain distance from each other. In particular, the at least two receiving antennas are constituted by at least two physical antennas. Alternatively, the at least two receiving antennas are constituted by a single antenna which is moved between different receiving positions by a suitable mechanism, e. g. a revolving mechanism. Accordingly, a moving receiving antenna constitutes "at least two receiving antennas" in the sense of the present invention.

In a preferred embodiment, range Doppler maps are generated from the received radio waves. Range Doppler maps relate the distance of targets from a receiving antenna to their relative velocity away from or towards the receiving antenna. Accordingly, signatures relating to body movements may be identified based on range Doppler data.

As an alternative to radar other technologies such as LiDAR, ToF or laser ranging may be used.

Preferably, a two-dimensional position, in particular a three-dimensional position, of the received electromagnetic waves is considered when determining the movement activity level and/or when analyzing the received electromagnetic waves to obtain the information on the body position.

This allows for spatial resolution of the received electromagnetic waves and thus inter alia for an easy distinction between signals reflected from different patients present in a single monitoring volume (e. g. a hospital room). The position of the patients may be automatically determined based on identified vital signs and/or positionally clustered activity information. As an alternative, the expected position of patients, e. g. the (present) position of beds in a room, may be manually entered in a user interface of the system.

If available, signals obtained from a plurality of sensors may be taken into account to determine information on a body position of the patient. For instance, a two or more radar sensors providing three-dimensional data are arranged at different points in a room. Due to the relative position and orientation of the sensors and the patient as well as obstacles within the room, signal propagation may be differently affected, whereby a particular sensor allows for a better detection of the person in a first body position, whereas another sensor allows for a better detection of the person in different second body position. Accordingly, by using two or more sensors, the reliability of the inventive method may be further enhanced.

When information on the position of the origin of the reflections is available, various analyses are enabled such as relating to the density, shape, distribution, grouping or clustering of reflectors.

Preferably, an at least two-dimensional range Doppler map is obtained from signals received by at least two of the receivers and in that positions are assigned to detected movements. This allows for assigning activity levels to certain subvolumes of the monitored volume, and specific information may be obtained by analyzing the amplitude and/or phase of electromagnetic waves received from a certain subvolume or a group of certain subvolumes (e. g. relating to a certain patient or body region).

In a preferred embodiment, information relating to different parts of the patient's body is independently processed. This allows for obtaining more detailed information and for generating information related to the activity level or repositioning frequency of individual body parts, e. g. individual limbs. As an example, this allows for a risk assessment for bedsore specific to certain body parts.

In a preferred embodiment, the method includes analyzing a temporal progression of data obtained from the received electromagnetic waves to identify a signature relating to vital signs of the patient and by obtaining vital sign information from the identified signature.

The vital signs may relate to physiological functions of the patient causing (micro-) movements, including heartbeat, breathing and digestion.

In order to identify and processing the signatures, in particular Doppler and/or micro-Doppler information obtained from the received electromagnetic waves may be processed.

The vital sign information may be processed together with the information on the body position and/or it may be used for general monitoring purposes. In some cases, corresponding local sensors potentially bothering the patient may be dispensed with, thus improving the patient's comfort.

It is important to note that the signals relating to the Doppler shifts caused by the micro-movements are affected by the body position as well, namely in two aspects: First of all, physiological processes such as breathing may be affected by the body position, e. g. the amplitude of the breathing movement measured on the outside of the body may be smaller in a prone position than in a supine or lateral position. Secondly, the body position affects reflection as well as absorption of the relevant signals carrying the Doppler information. Accordingly, processing micro-Doppler information may contribute to an improved precision of the determination of the body position.

In a preferred variant of the inventive method, a position of a chest region of the patient is identified based on a breathing signature in the received electromagnetic waves. This is done based on the received electromagnetic waves relating to an activity level classified in the at least one low activity level class, as the identification of the breathing movement is much more reliable without superimposed (gross) body movements. Preferably, identification of the chest region is repeated in regular intervals and/or if a positional change of the patient is detected using methods as described above.

Preferably, movement points originating from the patient are identified in the received electromagnetic waves. Such movement points are generated from the received electromagnetic waves, e. g. by the radar system. Each such movement point represents a movement detected in the received electromagnetic waves. Beside the the 2- or 3-dimensional position of the movement its velocity and direction (i. e. a movement vector) are assigned to the respective movement point. In particular, the movement points are made available at regular time intervals ("frames").

Preferably, all movement points originating from the patient are collected during a first sample period and clustered to obtain one or several clusters in a position space. In particular, the bounds of a person (i. e. the three-dimensional volume in which all movement of the individual person was detected within a given period of time) are defined to be the convex hull surrounding all the movement points which were classified to belong to that person. Those bounds are continuously adjusted as new movements from that person are detected (i. e. the person moved a body part which was still before).

Advantageously, the first sample period is chosen to correspond to an average time of a breathing cycle in an inactive state of the patient, e. g. about 10 seconds. This value may be predetermined or dynamically adjusted based on the monitoring of the patient.

Preferably, the movement points are collected in three dimensions and clustered by a suitable clustering algorithm. They include inter alia available algorithms for the clustering of point clouds based on unsupervised learning.

Subsequently, each cluster is preferably classified according to its geometrical shape into a torso candidate class or a non-torso candidate class. The criteria for classification may relate to the shape itself, to absolute dimensions and/or to relative measures such as aspect ratios. Positional relationships between the clusters may be taken into account as well. Classification may be effected by supervised or unsupervised learning approaches or by conventional techniques, based on metrics such as the ones mentioned above, obtained from the clusters.

Preferably, the movement points are periodically collected and for each of the clusters a single value is calculated for all the movement points assigned to the respective cluster, the single value representing an activity level in the respective cluster.

In particular, the single value is calculated from a number of movement points collected and absolute velocities of each of the movement points.

These single values are collected over a second sample period. In particular, the second sample period covers a number of breathing cycles, e. g. 5-6 breathing cycles, corresponding to about 1 minute.

In a subsequent step, a frequency analysis is preferably performed over the collected single values and each of the clusters is classified into a chest candidate class or a non-chest candidate class, based on the result of the frequency analysis.

The frequency analysis may be based on a Fourier transform (DFT/FFT), Wavelet Transform or Z-transform. Breathing movements lead to frequencies of about 0.07-0.17 Hz. The stronger such frequencies are present in the frequency domain, the higher the probability is that the respective cluster relates to the person's chest.

In most cases, in the frequency domain one of the clusters will show clear indications of respiratory movement, while the other clusters will be free of such signs. If none of the clusters is classified into the chest candidate class, the analysis may be repeated. If the result persists, an alarm may be triggered. If more than one cluster is classified into the chest candidate class, the analysis may be repeated as well. In addition it may be checked whether the two or more clusters in the chest candidate class are actually part of a superordinate "chest" cluster. In this case, the clusters may be fused together into a single cluster or one of the candidate clusters may be chosen to represent the patient's chest.

Instead or in addition to the results of the frequency analysis, information on the geometry of the clusters may be taken into account when identifying the chest region.

Alternatively, not only the single values calculated for the clusters are taken into account for the frequency and breathing analysis, but the information is obtained directly from Range Doppler information relating to the respective cluster. In particular, the breathing rate as well as the heart rate may be obtained from phase information of the Doppler signals.

Instead of or in addition to the breathing movements, movements relating to the person's heartbeat may be identified and respective information may be processed to identify the person's chest. As a matter of course, the relevant frequencies will be higher, e. g. in the range of 0.8-1.4 Hz. Similarly, the first and second sample periods may be chosen differently, e. g. 1-2 s and 5-10 s, respectively.

Preferably, information relating to the chest region and information relating to other regions of the patient and a positional relationship between the chest region and the other regions are processed to obtain the information on the body position of the patient.

In particular, the chest area is defined as the convex hull around all the movement points in the chest cluster plus a small margin. Movement points from this "chest area" are now being collected separately from the rest of the movement-points from that person, deemed to relate to extremities. The positional relationship of the extremities and the chest/torso provides valuable information relating to the person's body position.

Other advantageous embodiments and combinations of features come out from the detailed description below and the entirety of the claims.

BRIEF DESCRIPTION OF THE DRAWINGS

The drawings used to explain the embodiments show.

In the figures, the same components are given the same reference symbols.

PREFERRED EMBODIMENTS

In the following, an embodiment of the invention is described, the described example relating to the monitoring of patients in a hospital environment. The general principles may be applied to other fields of application.

Figure 1:
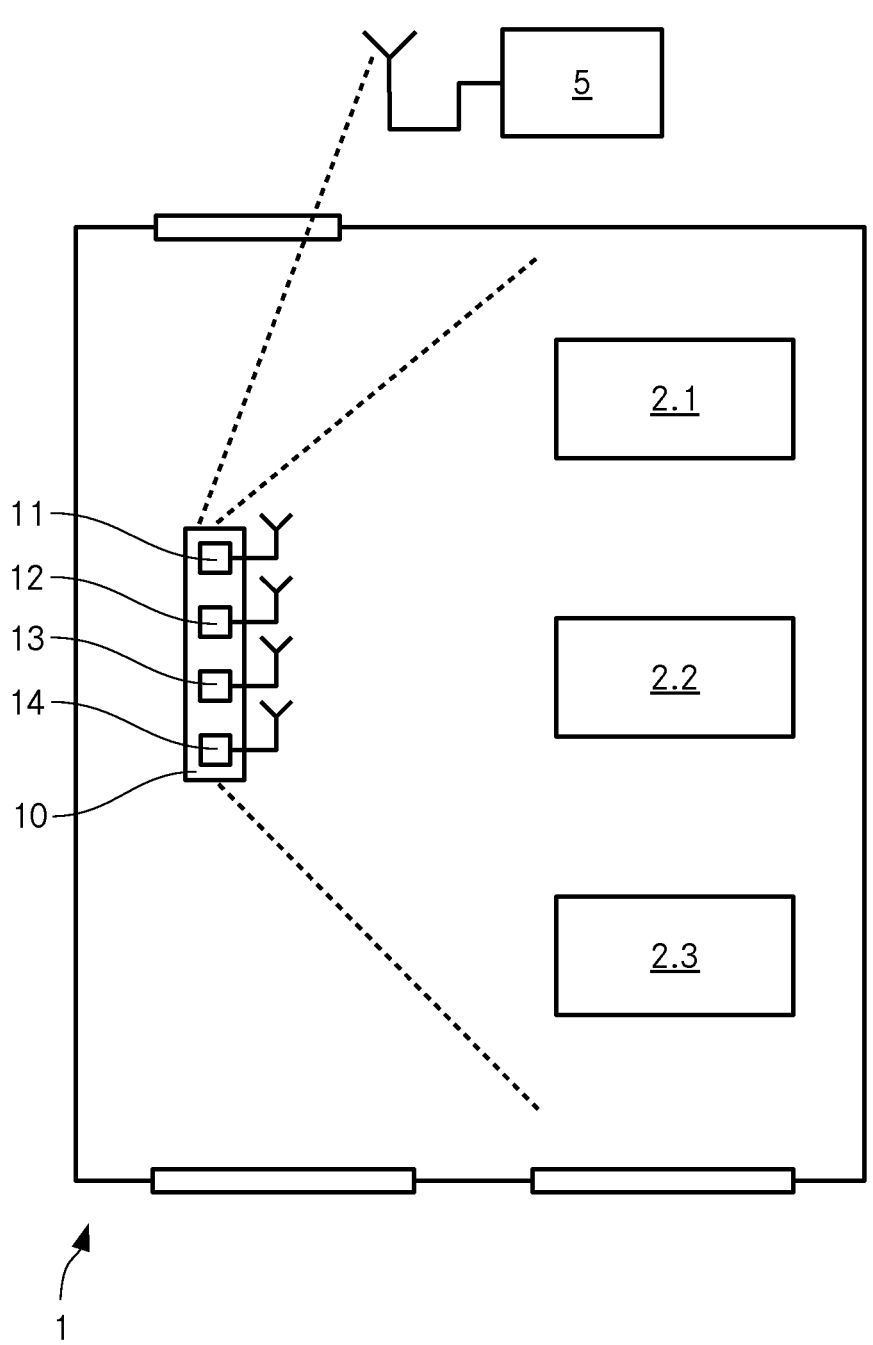
FIG. 1 A schematic representation of a hospital room with an embodiment of an inventive radar device installed.

The FIG. 1 is a schematic representation of a hospital room with an embodiment of the inventive system installed. Three beds 2.1, 2.2, 2.3 are placed in hospital room 1, along one of the side walls. The radar device 10 is attached to the ceiling of the room 1, its vertical distance to the support surfaces of the beds 2.1 . . . 3 is about 2-3 m. The radar device 10 comprises a transmitter 11 and three receivers 12, 13, 14. The transmitter 11 and the three receivers 12, 13, 14 are arranged within a housing of the radar device 10 in a certain distance from each other such that differences with respect to incoming signal phase are caused. Accordingly, the housing provides a certain linear extension. The radar device 10 is described in more detail below, with respect to FIG. 2.

The basically cone-shaped monitoring volume covered by the radar device 10, depicted by dashed lines, covers all the three beds 2.1 . . . 3. In addition to the transmitter 11 and the receivers 12, 13, 14, the radar system 10 comprises a power supply, acquisition and processing electronics as well as an interface for exporting radar data to further devices; the radar device 10 is connected to a central server 5 by means of a wireless communication link.

The radar device 10 may provide data on different processing levels, i. e. raw radar data, angle data, range Doppler maps and/or even lists of persons with assigned positions, activity and vital sign information. Depending on the level of detail of the processed information, more or less further processing steps are carried out by the server 5. The server 5 is also used for displaying and/or storing the obtained data. It may further be used for configuring the radar system and for controlling active devices for assisting the patient's repositioning, e. g. inflatable mattresses.

Figure 2:
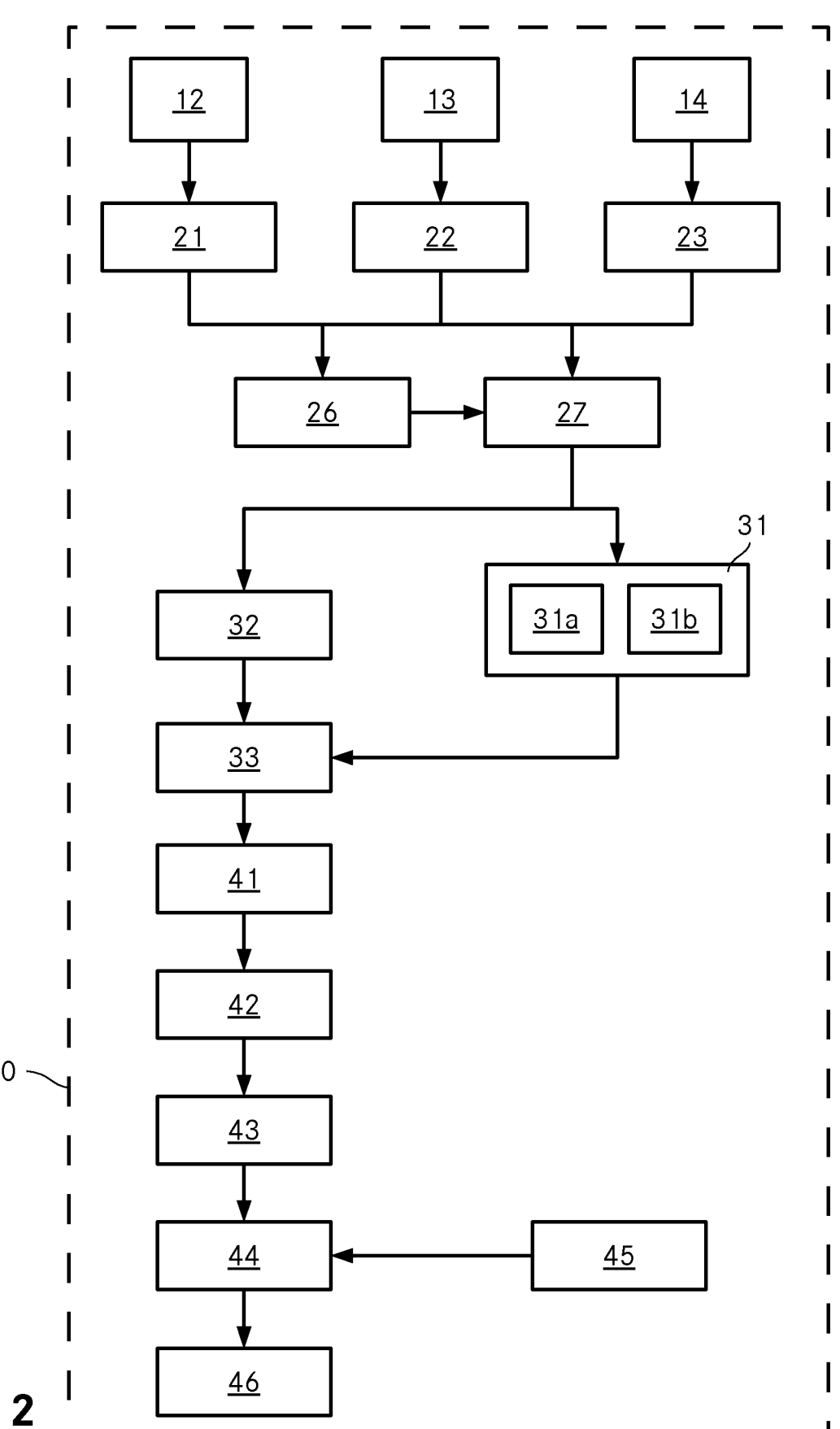
FIG. 2 a schematic block diagram of the radar device.

The FIG. 2 is a schematic block diagram of a radar device according to the invention. The device includes a MIMO UWB radar system 10 comprising a sender 11 and three receivers 12, 13, 14. The center frequency of the radar system is between 2 and 75 GHz.

The three receivers 12, 13, 14 provide radar data to 1-dimensional range Doppler modules 21, 22, 23 of the radar device 10. These modules deliver range Doppler data to a computing module 26 for calculating the angles of arrival based on the phase differences between the signals of the three receivers 12, 13, 14. Furthermore, a 3-dimensional Doppler map is generated by a further computing module 27 based on the range Doppler data as well as on the angles of arrival.

Basically, the range Doppler maps may be generated by the range Doppler modules, based on the raw radar data of several transceivers by the following steps:

1. The radar data is received by the processor from the transceivers. The data is organized in a matrix, where the columns correspond to separate, consecutive chirps. The lines of a given column represent the samples of the given chirp.

2. A matrix of a symmetric window function is generated, where the window length corresponds to the samples per chirp (number of lines) and the number of chirps (number of columns).

3. For each transceiver, a (1-dimensional) range Doppler map is calculated based on an average of a succession of radar signals (to reduce noise), windowed by the window function, applying a 2-dimensional Fourier transformation and shifting zero Doppler to the middle of the x axis.

4. Now, the phase difference may be obtained from two range Doppler maps $M_{RD,1}$, $M_{RD,2}$ by calculating $M_{RD,1} \cdot \overline{M_{RD,2}}$. This step may be repeated or generalized to more than two transceivers.

5. From this product or these products, respectively, the angles of arrival may be calculated from the phases of the matrix elements.

The range Doppler data is fed to an identification module 31 for the identification of signatures relating to the breathing of a human (submodule 31a) as well as for the identification of signatures relating to the heartbeat of a human (submodule 31b). This step includes the classification of sequences of range Doppler signals relating to detected objects. The sequences cover an interval having a duration that is substantially longer than the expected periodicity of the signals (e. g. at least 5 s for the detection of heartbeat and at least 20 s for the detection of breathing).

The identification may be done by several methods, including machine learning (e. g. deep Neural Network) and/or pattern matching algorithms. The result relates to probability of recognizing human breathing and/or heartbeat.

The identification may be based on Micro-Doppler data, where effects of a first type of motion (caused by breathing) superimposed to a second type of motion (caused by the heartbeat) are eliminated, such that the motions of the second type are more clearly discernible.

Furthermore, the range Doppler data as well as the angles of arrival are fed to a positioning module 32, setting up a list of locations related to identified subjects. Next, the list of locations and the identified signatures are correlated in a correlation module 33 to obtain a list of detected subjects containing values for the relative position ($x_{rel}$, $y_{rel}$, $z_{rel}$) and information on vital signs obtained from the range Doppler data by the computing module 27.

In a further step, a boundary box is automatically defined around each of the relative positions, the size of which chosen to encompass the entire support surface of a patient's bed but not the support surfaces of neighboring beds. Accordingly, the system automatically adapts to changing circumstances due to e. g. the repositioning of patient beds, new patients, patients leaving the room, etc. The initial setup of the radar device requires only a very short time. This also applies to repositioning of the radar device, even when the device is moved to another room (e. g. where the device is only temporarily attached to the ceiling or wall or positioned e. g. on a stand).

Reflected signals originating from within the defined boundary boxes are assigned to the respective subject and processed to obtain the information on the respective body position. In a most simple case, the signals coming from a certain boundary box are summed. However, a more detailed analysis is possible.

Next, for each of the subjects the current movement activity level is determined from the respective signals by a signal processor 41. This activity level may correspond to the variance of the IQ signal summed up for the respective bounding box. If this value exceeds a certain threshold, the subject is classified by classifier module 42 as presently active, if not, the subject is classified as presently non-active. The threshold may depend on the specific radar system 10 and its arrangement in the hospital room and relative to the beds 2.1 . . . 3. Accordingly, the threshold is determined during a calibration process of the system. Automatic recalibration is possible, e. g. during intervals when no patient is present in the monitored area.

In case of an active classification that is confirmed during a certain first time period (e. g. 2 seconds), the status of the subject is switched to "active" or kept at "active"—in case of such a switch, the past interval according to the first time period is retroactively assigned to active status. If the status is "active" and the classification has been non-active for a certain second time period (e. g. the past 10 seconds) the status is switched to "non-active". Accordingly, every point in time is assigned to an "active" or "non-active" interval, wherein active and non-active intervals follow each other alternately.

Next, the signals obtained in non-active intervals are analyzed by analyzer module 43. As an example, for doing so, the median of 10-second-blocks may be calculated. This quantity then serves as a signature for the patient's body position in the low activity interval. The signatures of each two consecutive low-activity intervals are compared by calculating a distance using a suitable distance metrics. In a further step, based on the distance, a probability value is calculated, relating to the probability of a body position change between the two consecutive low-activity intervals.

In addition, a correlation module 44 accesses a database 45 storing signature information relating to different body position. A correlation between the signature of a low activity interval and each of the signatures stored in the database 45 is calculated in order to assign each of the low activity intervals to a body position.

The body position may be determined using another process including the following steps, carried out during an inactive phase:

1. The bounds of the monitored person, i. e. the three-dimensional volume in which all movement of the person was detected for a given period of time, are determined by the convex hull which surrounds all the movement points which were classified to belong to that person. Those bounds are adjusted continuously as newly captured movements from that person are received that relate to movement of a body part which was still before during a certain time.

2. All the movement-points of the person are collected over the average time of a breathing cycle in the inactive state (ca. 10 seconds) and are clustered using a dedicated clustering algorithm.

3. Each cluster is evaluated according to its geometrical three-dimensional shape. Clusters which their shape and size cannot be representing a chest (e.g. too large, too long) are filtered out.

4. For each remaining cluster the movement-points are collected every 125 ms and a single value is calculated. This single value takes into account the number of points collected in this time period as well as the absolute velocity of each point. It is a measure for the activity level in the respective cluster.

5. The single values for each cluster are collected over a period of time representing 5-6 breathing cycles in inactive state (ca. 1 minute).

6. A Fourier transform is performed over the collected indexes for each cluster to detect the frequencies in the data. The stronger the ~0.07-0.17 Hz frequency is present, the higher the probability is, that the cluster is the person's chest.

7. Now, the chest area is defined as the convex hull around all the movement points in the chest cluster plus a small margin. Movement points from this chest area are now being collected separately from the rest of the move-ment-points from that person ("extremities").

The body position is obtained from the number, size, shape and position (including the positional relationships) of the identified clusters, taking into account the assignment of the chest/torso. The person is continually tracked. If the position of the person changes, the chest-detection process is repeated.

Based on the number of position changes and/or the determined body positions a risk for bedsore may be calcu-lated by a risk module 46. In addition to the general risk assessment, specific information on body portions at risk for pressure ulcers may be provided to the nursing staff. This ensures that these body portions are carefully examined and necessary measures are taken if required.

Basically, the steps described above are repeated to have updated information on the situation. The repetition/update frequency for the different phases may be different. The radar measurements are repeated frequently, with a period of 1 s or less. The same applies to the steps leading up to the determination of the activity level. Steps such as defining the boundary box may happen less frequently. Finally, the assessment of the risk for bedsore may happen e. g. once every hour or even only on demand if the nursing staff is about to update the nursing plan for a given patient.

Figure 3:
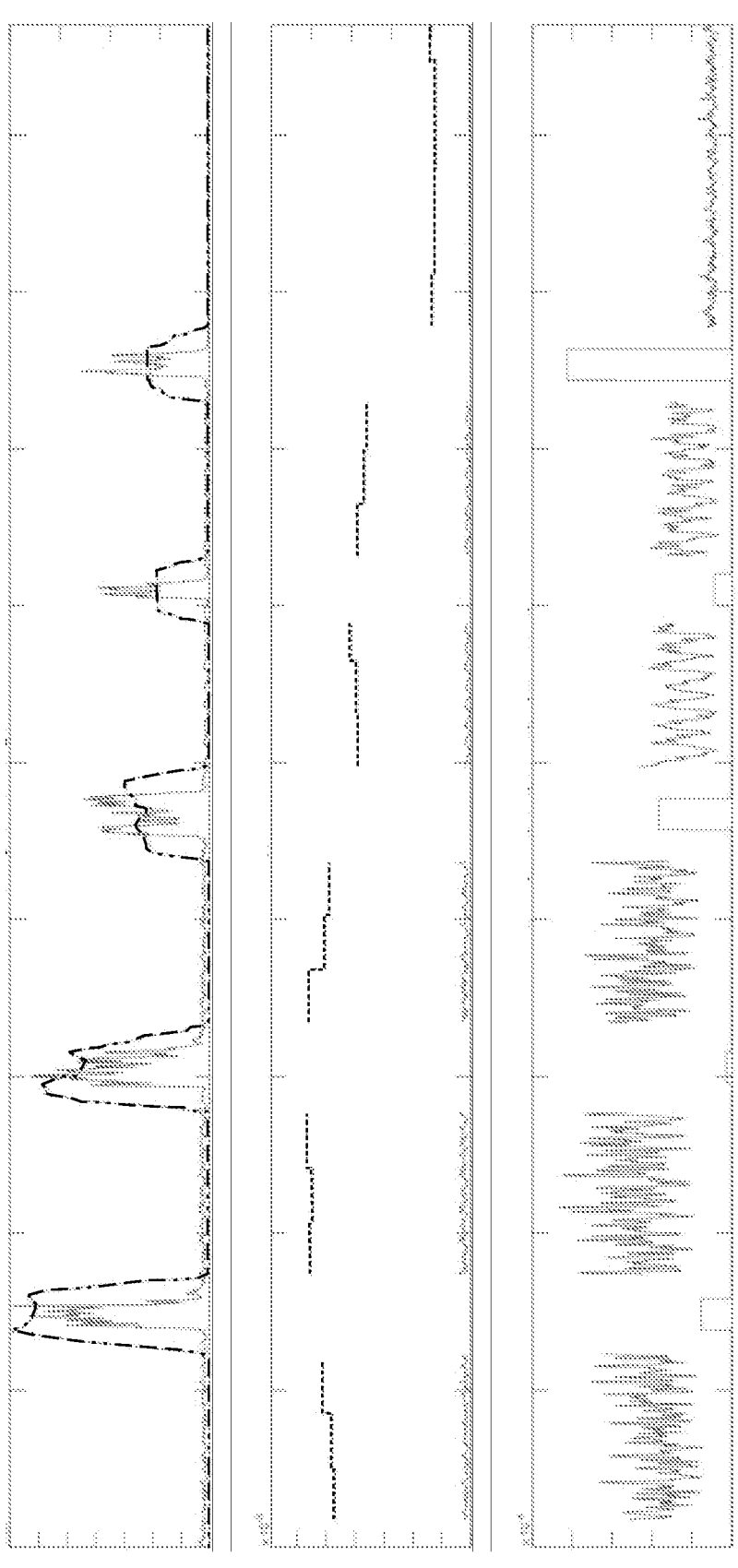
FIG. 3 an exemplary temporal sequence of activity signals obtained by the device.

The FIG. 3 shows an exemplary temporal sequence of activity signals obtained by the system. It relates to a monitoring volume covering the bed with a lying patient asleep. The charts cover a time interval of approximately 5 minutes, including 5'000 frames at 17 fps. The upper chart shows a measure for the movement activity obtained from all the reflection points within a boundary box delimiting the monitoring volume. The five peaks relate to movement events, where the patient exhibits stronger movements. The dashed-dotted curve indicates the variance of the first curve.

The signal is partitioned into segments of high variance and segments of low variance. For the further analysis, only the segments of low variance are considered. These seg-ments relate to isolated phases of low activity (micro-movements/vegetative phases). In the lowest curve, the activity signal in these phases is shown in more detail. The respective phases are analyzed with respect to their statis-tical characteristics, by calculating measures such as aver-age/median value, variance etc. As an example, the dashed lines of the middle chart show the median of 10-second blocks within each phase.

These characteristics are compared between the consecu-tive phases. Substantial differences point to a high probabil-ity of a change of position in between the phases. Accord-ingly, it may be assumed with a high confidence that the patient has changed its position. The bars in the lowest chart indicate the probability of a change of position. Indeed, the monitored patient has substantially changed his position between the $3^{rd}$ and the $4^{th}$ phase (from a supine position to a prone position) as well as between the $5^{th}$ and the $6^{th}$ phase (from the prone position to a lateral position). In both cases, the determined probability exceeds a certain threshold. By suitably choosing this threshold, changes of position may be reliably detected from the received radar signals.

The invention is not restricted to the described embodi-ments. As an example, instead of a MIMO UWB radar system usual phased arrays may be used and/or wideband radars having smaller bandwidths such as about 150 MHz.

The frequency of the radar system may be adjusted to the purpose of the system. As an example, higher frequencies of up to 120 GHz or more may be used as long as the required penetration capacity is achieved.

In three-dimensional systems, more than three receiving antennas may be employed. In two-dimensional systems, two antennas may be sufficient. In principle, there may be a single transmitting antenna or a plurality of transmitting antennas. Furthermore, as mentioned above a plurality of antennas may be replaced by a moving (e. g. rotating) antenna that effectively provides multiple receiving (and/or sending) locations.

Some of the functions or steps are not mandatory. As an example, the setup of the radar device, including the defi-nition of the boundary boxes, may be manual, and vital signs such as breathing and heartbeat do not necessarily have to be monitored in the context of the inventive system.

In summary, it is to be noted that the invention provides a method for monitoring a recumbent patient to obtain information on a body position of the patient that does not bother the patient and provides accurate results.

What is claimed is:

1. A method for monitoring a recumbent patient to obtain information on a body position of the patient, comprising the steps of:

a) emitting electromagnetic waves by a sender arranged in a distance from the patient;

b) receiving electromagnetic waves reflected by the patient by a receiver arranged in a distance from the patient;

c) determining a movement activity level from an amplitude and/or phase of the received electromagnetic waves;

d) classifying the activity level into at least one high activity level class and into at least one low activity level class, wherein gross motor movements of the patient are classified into the at least one high activity level class; and e) analyzing the amplitude and/or phase of the received electromagnetic waves relating to an activity level classified in the at least one low activity level class to obtain the information on the body position of the patient, wherein the information on the body position of the patient is a signature of a temporal progression of values obtained from the amplitude and/or phase of the received electromagnetic waves relating to the activity level classified in the at least one low activity level class, and the obtained signature is compared to stored signatures obtained for past time intervals, wherein at least some of the stored signatures are assigned to specific body positions;

wherein the electromagnetic waves are radio waves and wherein the sender and receiver are part of a radar system, and wherein range Doppler maps are generated from the received radio waves and the activity level is obtained from a variance of a velocity obtained from the received electromagnetic waves by calculating an index of dispersion of range-Doppler matrices of consecutive time intervals.

2. The method as recited in claim 1, wherein the classified activity levels are assigned to consecutive time intervals.

3. The method as recited in claim 1, wherein the assignment of specific body positions to the stored signatures is carried out by using a machine learning method, the machine learning method comprising either of:

i. training data including various captured or simulated signatures and the respective body positions;

ii. a training phase where the body positions are identified by pressure sensors, video data, acoustic information, or data obtained from wearables; and iii. a training phase where the body positions are manually entered.

4. The method as recited in claim 1, wherein the radar system is a wideband radar system.

5. The method as recited in claim 1, wherein a two-dimensional position of the received electromagnetic waves is considered when determining the movement activity level and/or when analyzing the received electromagnetic waves to obtain the information on the body position.

6. The method as recited in claim 4, wherein an at least two-dimensional range Doppler map is obtained from signals received by at least two of the receivers and in that positions are assigned to detected movements.

7. The method as recited in claim 5, wherein information relating to different parts of the patient's body is independently processed.

8. The method as recited in claim 1, comprising the further step of analyzing a temporal progression of data obtained from the received electromagnetic waves to identify a signature relating to vital signs of the patient and by obtaining vital sign information from the identified signature.

9. The method as recited in claim 8, wherein a position of a chest region of the patient is identified based on a breathing signature in the received electromagnetic waves.

10. The method as recited in claim 9, wherein movement points originating from the patient are identified in the received electromagnetic waves and in that all movement points originating from the patient are collected during a first sample period and clustered to obtain one or several clusters in a position space.

11. The method as recited in claim 10, wherein each cluster is classified according to its geometrical shape into a torso candidate class or a non-torso candidate class.

12. The method as recited in claim 10, wherein the movement points are periodically collected and for each of the clusters a single value is calculated for all the movement points assigned to the respective cluster, the single value representing an activity level in the respective cluster.

13. The method as recited in claim 12, wherein the single value is calculated from a number of movement points collected and absolute velocities of each of the movement points.

14. The method as recited in claim 12, wherein the single values are collected over a second sample period.

15. The method as recited in claim 14, comprising the further step of performing a frequency analysis over the collected single values and classifying each of the clusters into a chest candidate class or a non-chest candidate class.

16. The method as recited in claim 7, wherein information relating to the chest region and information relating to other regions of the patient and a positional relationship between the chest region and the other regions are processed to obtain the information on the body position of the patient.

17. A method for obtaining information for assessing a patient's risk for bedsore, comprising the following steps:

a) obtain information on a body position of the patient using a method as recited in claim 1 at successive points in time;

b) processing the information to obtain at least one of the following:

a frequency of repositioning activities of the patient;

a distribution of body positions assumed by the patient.

18. The method as recited in claim 1, wherein a three-dimensional position, of the received electromagnetic waves is considered when determining the movement activity level and/or when analyzing the received electromagnetic waves to obtain the information on the body position.

\* \* \* \* \*